United States Patent [19]

Vanderpool

[11] 4,432,545

[45] Feb. 21, 1984

[54] NON-LETHAL COCK FIGHTING SYSTEM

[76] Inventor: Charles C. Vanderpool, R.D. #1, Waverly, N.Y. 14892

[21] Appl. No.: 373,577

[22] Filed: Apr. 30, 1982

Related U.S. Application Data

[63] Continuation-in-part of Ser. No. 173,058, Jul. 28, 1980, abandoned.

[51] Int. Cl.³ ............................................. A01K 29/00
[52] U.S. Cl. ...................................... 273/1 GC; 2/18; 119/29; 272/76; 273/1 F
[58] Field of Search ................. 273/1 GC, 1 ES, 1 F, 273/374, 181, 184 R; 2/18, 425; 272/76; 340/323 R; 119/29, 143, 144, 1; 455/100

[56] References Cited

U.S. PATENT DOCUMENTS

| | | | |
|---|---|---|---|
| 2,669,389 | 2/1954 | Mesi et al. | 340/323 X |
| 2,916,287 | 12/1959 | Davey | 273/1 F |
| 3,224,412 | 12/1965 | Fuentes, Jr. | 119/144 X |
| 3,302,214 | 2/1967 | Yuritch | 272/76 X |
| 3,380,305 | 4/1968 | Charell | 273/1 GC X |
| 3,771,786 | 11/1973 | Bouldin | 273/1 F X |
| 4,088,315 | 5/1978 | Schemmel | 272/76 |

FOREIGN PATENT DOCUMENTS

| | | | |
|---|---|---|---|
| 2532692 | 2/1976 | Fed. Rep. of Germany | 273/1 F |
| 2741090 | 3/1979 | Fed. Rep. of Germany | 273/1 F |
| 580169 | 7/1958 | Italy | 273/1 F |
| 10226 | of 1911 | United Kingdom | 273/1 F |
| 1120613 | 7/1968 | United Kingdom | 273/1 F |
| 267403 | 4/1970 | U.S.S.R. | 272/76 |
| 519200 | 7/1976 | U.S.S.R. | 273/1 F |
| 598613 | 3/1978 | U.S.S.R. | 272/76 |

OTHER PUBLICATIONS

Scientific American 8/32, p. 105, Boxing Match Scoreboard.

Primary Examiner—Paul E. Shapiro
Attorney, Agent, or Firm—Charles S. McGuire

[57] ABSTRACT

A pair of sparring gloves or muffs are attached to each leg of a pair of fighting cocks over the natural spur area. The muffs incorporate a member slideably movable along the axis of the natural spur in response to blows struck substantially along this axis. A plurality of switch means are successively actuated in response to movement of the slideable member by various increments of distance, commensurate with the force of the blow. Signals are generated and transmitted to a remote location by transmitters actuated by the switches and attached to the skin at posterior areas below the tail feathers of each bird. The signals are received at the location outside the fighting pit and used to increment counters indicative of the scores of the respective birds, which are weighted according to the force of the blows struck and visually displayed to the spectators.

7 Claims, 3 Drawing Figures

NON-LETHAL COCK FIGHTING SYSTEM

REFERENCE TO RELATED APPLICATION

The present application is a continuation-in-part of application Ser. No. 173,058, filed July 28, 1980, of the same inventor, now abandoned.

BACKGROUND OF THE INVENTION

The present invention relates to apparatus for conducting and scoring non-lethal cock fights and, more specifically, to special apparatus for attachment to the legs of fighting cocks and electronic means for implementing such apparatus to provide a novel and improved scoring system.

Cock fighting is an ancient sport in which male birds having very strong combative instincts are encouraged to attack one another, using as weapons either the spurs which grow naturally from the backs of their legs or metal barbs or other such spur substitutes. In any case, the winner is usually determined by either killing or injuring the opponent so severely that the fight cannot continue. Accordingly, the sport has been outlawed in many parts of the modern world.

Means have been proposed for conducting cock fights in a non-lethal manner, such as that disclosed in U.S. Pat. No. 3,771,786, for example. However, such means do not accurately reflect the actual outcome of the same fight conducted with actual or artificial spurs, since there is no way to distinguish the direction or force of blows struck. Other means incorporating force-indicating means have been employed for scoring human boxing matches, but these are unsuitable for use in cock fighting applications; furthermore, such systems are not limited to actuation by blows struck along only a single axis.

It is a principal object of the present invention to provide novel and improved apparatus for conducting and scoring cock fighting matches.

A further object is to provide apparatus for non-lethal cock fighting which discriminates among various forces of blows delivered by the combatants.

Another object is to provide apparatus for automatically scoring a non-lethal cock fight which registers points only in response to blows delivered substantially along the axis of the natural spur.

Other objects will in part be obvious and will in part appear hereinafter.

SUMMARY OF THE INVENTION

In accordance with the foregoing objects, the invention contemplates the mounting upon each bird of a pair of gloves or muffs in place of or in covering relation to the natural spurs or portion thereof. The muffs are mounted upon members which are biased to an outer position and moveable linearly along the spur axis in response to blows struck substantially along such axis and by a distance commensurate with the force of the blow. A plurality of switches within each mechanism are actuated by various increments of movement of the moveable member, thereby generating electrical signals which may be of distinguishable frequencies in accordance with the force of the blow, as well as by which leg of which bird the blow was delivered. The signals are transmitted, by means of transmitters mounted on the birds, preferably in a posterior area below the tail features, to a location remote from the fighting pit, where they are received and utilized to increment electronic counters. The scores accumulated on the counter, which may be weighted as desired by the force of the blows, displayed by rounds and/or cumulatively, or otherwise tailored to the desired situation, are visually displayed to the spectators.

DETAILED DESCRIPTION

Figure 1:
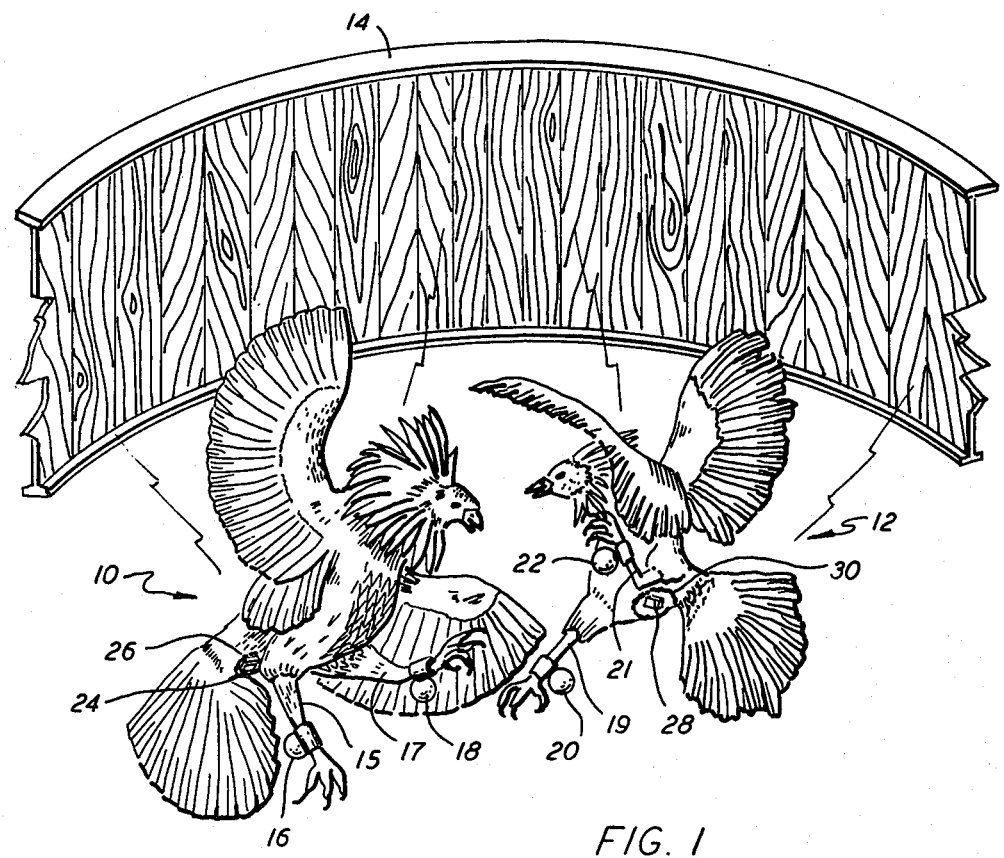
FIG. 1 is a perspective view of a pair of birds engaged in a cock fight employing the system of the present invention.

Referring now to the drawings, in FIG. 1 are shown a pair of fighting cocks 10 and 12 engaged in combat in the usual fighting pit surrounded by wall 14. Mounted upon the right and left legs 15 and 17, respectively, of birds 10 are muffs 16 and 18. Bird 12 is similarly equipped with muffs 20 and 22 on the right and left legs 19 and 21, respectively. Each of the muffs is mounted in the position where the natural spur would otherwise be located.

Muffs 16 and 18 are connected by wires extending up the legs of bird 10 to an electrical power source and signal transmitter 24 which is attached to a posterior area 26 below the tail feathers of bird 10. An electrical power source and signal transmitter 28 are mounted on the corresponding area 30 of bird 12. Preferably, the features are removed from areas 26 and 30, which are clipped or shaved to permit attachment of transmitters 24 and 28 directly to the birds' skins. Transmitters 24 and 28 are conventional form, capable of transmitting a plurality of different signal frequencies, as will appear more fully later. The transmitters may be attached to the birds by an appropriate harness or strap, or by a double-sided adhesive tape. The indicated area of attachment is virtually the only area which is seldom struck during a cock fight and is therefore most desirable to minimize the possibility of the transmitter becoming damaged or dislodged during a fight.

Figure 2:
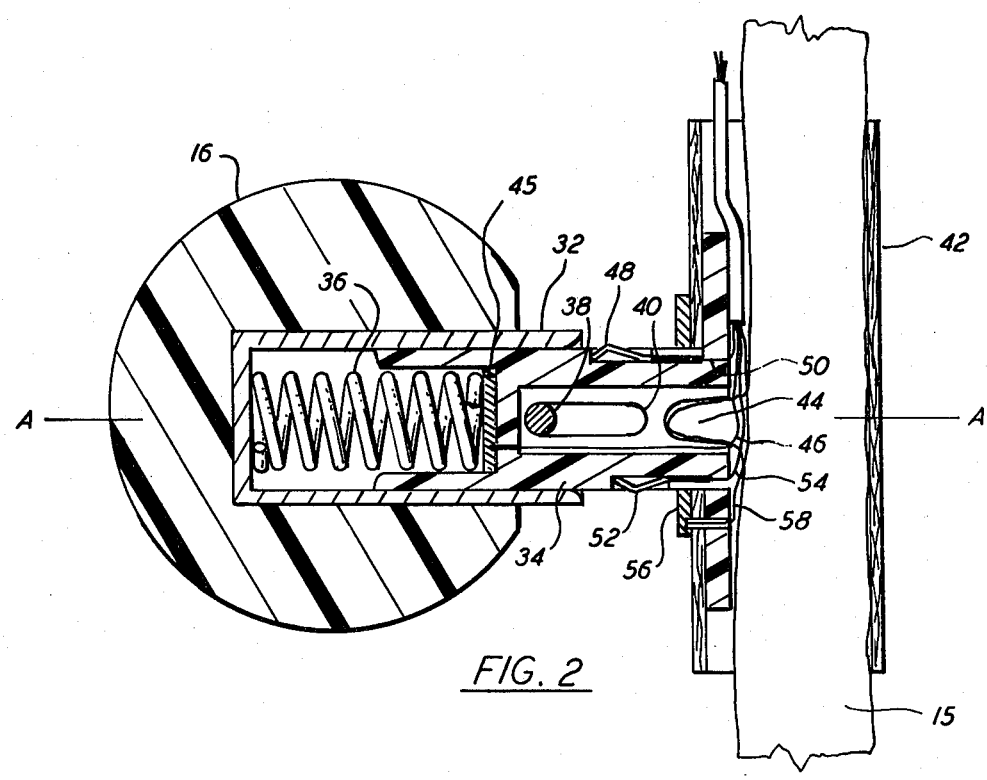
FIG. 2 is an enlarged, elevational view in vertical section of one of the switch means mounted upon the legs of each bird in FIG. 1.

Referring now to FIG. 2, muff 16 is shown in enlarged section with an associated force-indicating switch system, which is included in the same form in each of muffs 16 and 18, 20 and 22, the following description of muff 16 being applicable to each of the four muffs. Muff 16 is shown as essentially spherical, but may be elongated or of other desired shape, is attached to tubular member 32 which is slideable upon fixed support 24. Spring 36 biases member 32 to its outermost position with respect to support 34, defined by contact of pin 38 on member 32 with the outer end of elongated slot 40 in support 34.

The mechanism is mounted to the bird's leg, a fragment of right leg 15 of bird 10 being shown in FIG. 2, by a flexible element 42 which is wrapped about the leg and secured by string ties, or any other convenient means. Fixed support 34 is securely attached to flexible element 42, and thereby to the bird's leg, with the axis A—A of the natural spur aligned with the axis of slideable movement of member 32. The natural spur may be clipped or filed down to a portion of its original length, such spur portion being indicated in FIG. 2 by reference numeral 44 extending into the hollow interior of support 34, or the spur may be removed altogether; in any case the natural spur axis is aligned with the axis along which member 32 moves in response to a force applied to muff 16, as by a blow struck by the muff along the spur axis.

Tubular member 32 is constructed of a material having good electrical conducting properties and is connected through spring 36 and plate 45 to electrical lead 46 which provides a common line to power source and transmitter 24. Upon movement of member 32 by a first predetermined increment, it will come into electrical contact with spring contact 48 which is connected by lead 50 to the transmitter, serving to generate a signal which is transmitted to a receiver at a location remote from the fighting pit, as will be explained later in more detail.

Application of greater force to muff 16 along axis A—A, against the biasing force of spring 36, will move element 32 by a second increment to spring contact 52 which is connected to transmitter 24 by lead 54, resulting in the generating and transmitting of a second signal. Application of an even greater force moves element 32 into contact with plate 56 which is connected to transmitter 24 by lead 58, thereby generating and transmitting a third signal.

It is apparent at this point in the description that the invention provides a means for conducting non-lethal cock fighting with a reliable and accurate scoring system to determine which bird would have been the winner if the fight had been conducted in the traditional manner with the birds wearing spurs intended to injure or kill the opponent. This is made possible by the provision of a scoring system which registers points only in response to blows struck substantially along the natural spur axis, which are the only effective blows in a traditional cock fight. Furthermore, the scoring means discriminates among various forces of the blows struck along the spur axis by generating individual signals which distinguish increments of movement of a force-biased member along the spur axis.

The described system offers many possibilities for scoring and display within the present state of the art. For example, since an individual signal of unique parameters, such as frequency, is generated for each leg of each bird at various force levels, six separate numerical displays may be provided so that spectators are continually appraised of the number of blows at each force level struck by each leg of each bird. These displays may be by individual round and/or a cumulative display of total score over the course of an entire bout of multiple rounds provided. The scoring for blows at the higher force levels may be weighted more heavily, if desired, as by assigning one, three and five points for light, medium and heavy blows, respectively. If a less sophisticated, lower cost system is acceptable, in its simplest form it would be necessary to generate and transmit signals of only one frequency to increment a single counter for each bird. Such a system still would discriminate among the various forces of blows since two individual signals would be transmitted for a medium force below and three signals for a heavy blow; that is, in order for member 32 to contact plate 56 it must first contact spring contacts 48 and 52, generating a signal and registering a count upon each contact, whereby a medium blow would increment the counter and scoring display twice, and a heavy blow three times.

Figure 3:
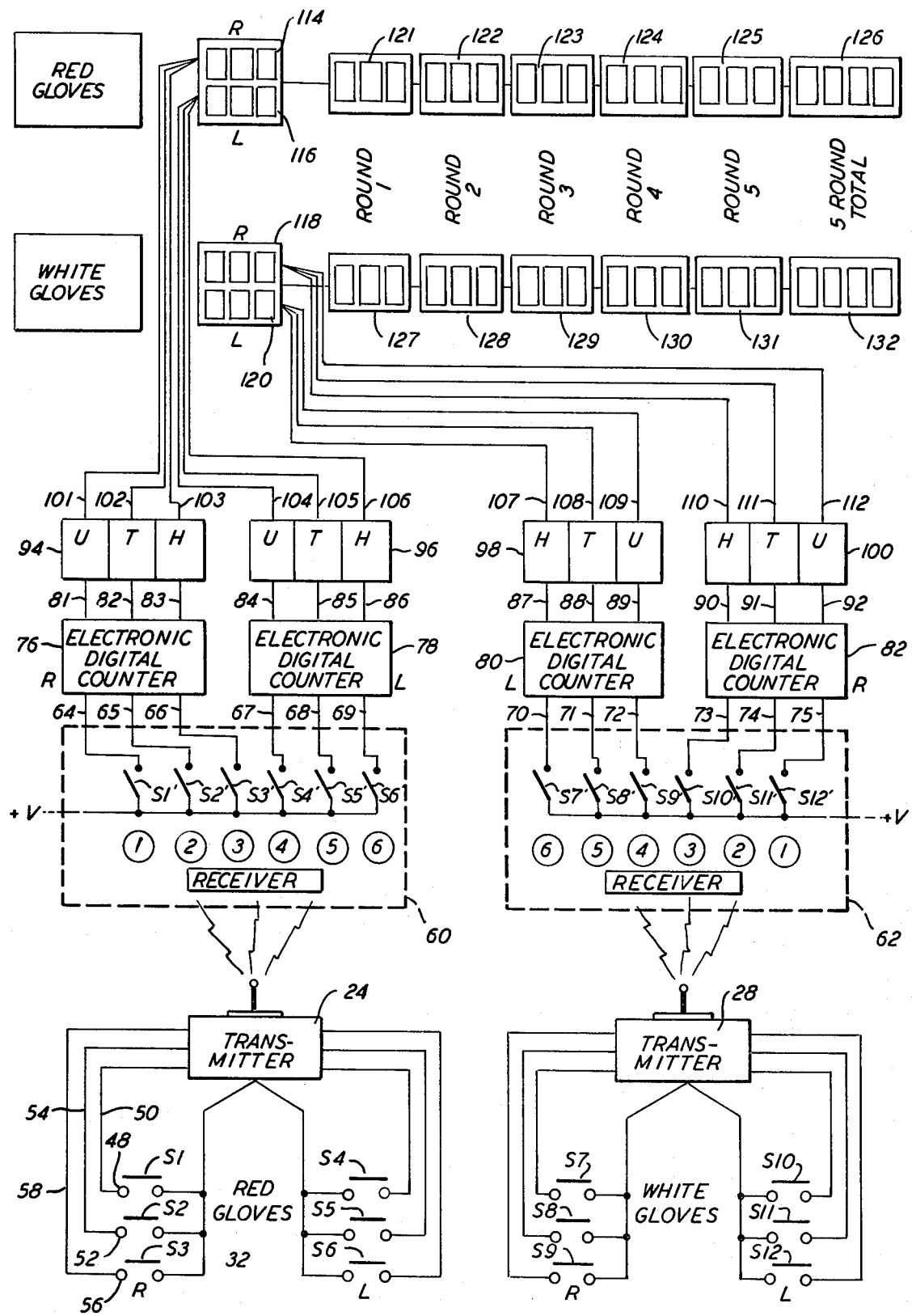
FIG. 3 is a schematic-block diagram of the electronic elements of a cock fight scoring system embodying the invention.

Although, as just indicated, the scoring and display possibilities are numerous and depend largely upon the level of discrimination and overall system cost desired, a representative system will now be described with reference to FIG. 3. Birds 10 and 12 are distinguished by the color of the muffs or gloves they wear, these being indicated as red and white, respectively. Reference numerals are applied to the schematic indications terminals and electrical leads for the right leg of bird 10 to correspond to those previously used in the description of these elements in FIG. 2. The three switches which are closed in response to light, medium and heavy blows along the spur axis of leg 15 of bird 10 are indicated at S1, S2 and S3. The switches associated with the mechanism on the left leg of bird 10 are denoted S4, S5 and S6, and the switches of the right and left leg mechanisms of bird 12 are denoted S-7 through S12.

Each of the switches S1–S6 and S7–S12 is connected to one frequency determining component in either transmitter 24 or 28 respectively. The frequency-determining components, although not shown, are well known in the art and might be frequency determining vibrating crystals each set at a discrete frequency spaced sufficiently in frequency from adjacent crystal's frequencies to facilitate discrimination in the receiver; or the switches S1 thru S12 might add shunt capacitance across an inductance to achieve a resonance in an oscillator and thus provide a transmitted signal on a frequency determined by the value of the inductance and the specific shunt capacitance. As with the vibrating crystals, the capacitance value must be selected so that the output frequencies will be sufficiently spaced apart for easy discrimination by the receiver.

Receivers 60 and 62 respectively are mounted in the scoring display above the fighting arena at a distance of no more than thirty to fifty feet from the transmitters 24 and 28. Due to the close proximity of transmitter and receiver, no extensive antenna system is required either at the transmitter or at the receiver. However, if an antenna is to be used it would be preferable to install the antenna at the receiver where an antenna could be more readily installed without interferring with the combatants.

Receivers 60 and 62 detect the frequency of the signal transmitted from transmitters 24 and 28. Since for each combatant there are three switches on each leg, the receivers 60 and 62 must be capable of simultaneously discrimating between and detecting two frequencies out of six. That is, one frequency for each scoring glove and two scoring gloves for each receiver. Also, it is important that the frequency bands selected for the combatant with the red gloves be properly selected and spaced apart in frequency to avoid interference between the signals from transmitters 24 and 28 at receivers 60 and 62. As an integral part of receivers 60 and 62, switches S1' through S6' in reciever 60 and switches S7' through S12' in receiver 62 are closed when a signal of appropriate frequency representing the predetermined force on the predetermined glove is activated by a blow struck along the respective spur axis.

When one of the aforementioned switches S1'–S12' is closed, a voltage signal is transmitted on a respective one of lines 62 thru 75.

It should be noted at this point that the aforementioned output lines 64 thru 75 are divided into groups of three, each group of three representing one striking glove. Therefore, it is possible to have simultaneous signals present on one line of each of the four following groups of three. Lines 64, 65 and 66 representing the right red glove, lines 67, 68 and 69 representing the left red glove, lines, 70, 71 and 72 representing the right white glove and lines 73, 74 and 75 representing the left white glove may have one of each group activated simultaneously. Also as discussed above, there may be a predetermined weighting of scoring value of relative force of blow. For example, a signal on line 64 may represent one point while a signal on line 65 may represent three points and a signal on line 66 may represent five points or any other selected sets of values. The same is true for the other three groups of lines discussed above. Lines 64 thru 75 are connected to electronic digital counters, 76, 68, 80 and 82 in the same groups of three as identified above. Each electronic digital counter accepting as an input three signal lines each signal line having a weighted scoring value when activated. Each of the electronic digital counters 76 thru 82 are well known devices available commercially from many sources.

When a signal appears on line 64 the output of digital counter 76 is incremented by one, whereas when a signal appears on line 65 the output of counter 76 is incremented by three, and when a signal appears on line 66 the output of digital counter 76 is incremented by five.

Electronic digital counters 76, 78, 80 and 82 include as an integral part thereof a binary to decimal converter circuit of a type which is well known in the art and readily available for commercial sources. The decimal outputs of digital counters 76, 78, 80 and 82 appear on lines 81-92. In each group of three lines outputed from one of the digital counters a first line such as line 81 represents a unit digit to the base 10, a second line such as line 82 represents a tens digit to the base 10, and a third line such as line 83 represents a hundreds digit to the base 10.

Although the embodiment of the electronic circuitry has been shown with only three digits, it is clear to those skilled in the art that additional counter stages could be added to expand the range of scoring without departing from the invention. Lines 81 thru 92 connect in groups of three to seven bar display drivers 94, 96, 98 and 100, respectively. In each of the seven bar display drivers, there is a section U which drives the display representing the units digit, a section T which drives the tens digit and a section H which drives the hundreds digit.

Seven bar display drivers are also circuits which are well known in the art and may be selected from many commercially available sources. For the sake of simplicity, the outputs of each of the seven bar disply drivers is shown as a single line although in fact generally there is an eight line cable require to drive each seven bar display. Lines 101 thru 112 respectively are connected to displays 114, 116, 118 and 120, in groups of three as described above, which display the instantaneous score of each glove during each round.

At the end of each round, the total for each pair of gloves is combined either manually or electronically and displayed for the proper round in display registers 121-125, for the red glove pair and 127-131 for the white glove pair. Similarly, the five round total is displayed in registers 126 for red gloves and 132 for white gloves.

Although the details of the adding of the scores for the right and left for each pair and the transfer of that total to the appropriate round display register, as well as the adding of the round totals for display in the give round total display registers 126 and 132 are not specifically set out and described with respect to the present invention, there are many systems both electronic and manual which are available to perform that function.

With regard to the scoring system, it has been mentioned that the simplest form would require only a single frequency for each bird, the force of the blows being weighted by the fact that one, two and three signals would be transmitted automatically be the disclosed switching means in response to light, medium and heavy blows, respectively. However, it often happens that blows are struck with both legs substantially simultaneously. It is preferred that a higher score be registered for blows struck with both legs than with only one leg. Therefore, in order to preclude the possibility of only one signal being registered in the scoring system when blows are struck simultaneously with both legs, it is preferred that separate frequencies be provided for the signals transmitted in response to blows struck by each leg of each bird.

From the foregoing, it may be seen that the objects of the invention are efficiently attained by a scoring system responsive to blows struck only along the spur axis of a pair of fighting cocks. The scoring system discriminates among a plurality of forces of the blows, registering higher scores for heavier blows. Even the lowest score is registered only in response to a solid blow, sufficient to move the switch means against a biasing force, whereby light blows which would be ineffective in a conventional cock fight are not scored at all. The biasing means, such as the spring of the disclosed embodiment, may be tailored as desired for various sizes, breeds, skill levels, etc. of the fighting birds.

What is claimed is:

1. Apparatus for conducting and scoring cock fights between two combating birds, said apparatus comprising, in combination:
    (a) individual switch means mounted upon each leg of each bird in place of or in covering relation to the natural spur, each of said switch means including a member movable along the axis of the natural spur in response to a blow struck substantially along said axis and by a distance commensurate with the force of said blow;
    (b) means for generating an individual electrical signal upon each movement of said member by at least a minimum increment of said distance, said signal having a parameter distinctive to each of said switch means and to a plurality of distinct increments of said distance;
    (c) means attached to the skin of each bird in a posterior area below the tail features where the feathers have been removed for transmitting said individual signals to a location remote from said birds;
    (d) signal processing means at said remote location for receiving said transmitted signals and for indexing a counter associated with each of said signals parameters in response to reception of each individual signal of said parameter; and
    (e) display means providing a visual indication of the accumulated count of each of said counters, thereby scoring the fight according to the number of blows of each increment of force struck by each leg of each bird.

2. The invention according to claim 1 and further including a stationary base member affixed to each leg of each bird, said movable member carrying one contact of said switch means and being movable with respect to said base member.

3. The invention according to claim 2 wherein a plurality of other contacts of said switch means are carried of said base member at axially spaced positions thereon.

4. The invention according to claim 3 and further including spring means biasing said movable member to an outermost position with respect to said base member, said movable member successively contacting each of said plurality of other switch means upon inward movement with respect to said base member against the biasing force of said spring means.

5. The invention according to claim 4 wherein said movable member includes a tubular element mounted for sliding movement upon said base member.

6. The invention according to claim 5 and further including a muff affixed to said tubular element in covering relation thereto.

7. The invention according to claims 3 or 6 wherein said plurality of other contacts are three in number.

* * * * *